United States Patent [19]
Bar-Cohen et al.

[11] Patent Number: 5,855,565
[45] Date of Patent: Jan. 5, 1999

[54] CARDIOVASCULAR MECHANICALLY EXPANDING CATHETER

[76] Inventors: Yaniv Bar-Cohen, 3721 Fuchsia St., Seal Beach, Calif. 90740; Willem Grandia, 919 Sunset Dr., Costa Mesa, Calif. 92627; Yoseph Bar-Cohen, 3721 Fuchsia St., Seal Beach, Calif. 90740

[21] Appl. No.: 861,374

[22] Filed: May 22, 1997

Related U.S. Application Data

[63] Continuation of Ser. No. 804,363, Feb. 21, 1997, abandoned.

[51] Int. Cl.⁶ ................................................. A61M 29/00
[52] U.S. Cl. ........................................... 604/104; 606/198
[58] Field of Search ........................... 604/104, 105–109, 604/280, 282; 606/191, 192, 194, 198

[56] References Cited

U.S. PATENT DOCUMENTS

| | | | |
|---|---|---|---|
| 5,263,963 | 11/1993 | Garrison et al. | 604/104 X |
| 5,358,496 | 10/1994 | Ortiz et al. | 604/104 X |
| 5,405,380 | 4/1995 | Gianotti et al. | 606/194 X |
| 5,456,667 | 10/1995 | Ham et al. | 604/107 |

OTHER PUBLICATIONS

Electroactive Muscle Actuators (EMA) JPL New Tech Rpt; Bar–Cohen et al Aug. 22, 1996.
Multi–Finger Electroactive Polymer Gripper (MEPG) JPL Inventor's Rpt Jan. 17, 1997.

*Primary Examiner*—John D. Yasko
*Attorney, Agent, or Firm*—Walter A. Hackler

[57] ABSTRACT

A cardiovascular mechanically expanding catheter apparatus in accordance with the invention generally includes a catheter having a mechanically expanding mechanism on a distal end thereof for dilating vessels such as arteries and other endoluminal structures and for the deployment of intraluminal stents. A permeable, mechanical dilating mechanism includes a pair of expanders which provide a radial force against walls of the vessel in response to a pulling or contracting longitudinal force on the dilating mechanism, by means of a cable for example. A set of adjacent quadrates are preferably provided for promoting uniformity of pressure by the expanders. An elastomer sleeve may be provided for protecting the vessel during the surgical procedure.

10 Claims, 5 Drawing Sheets

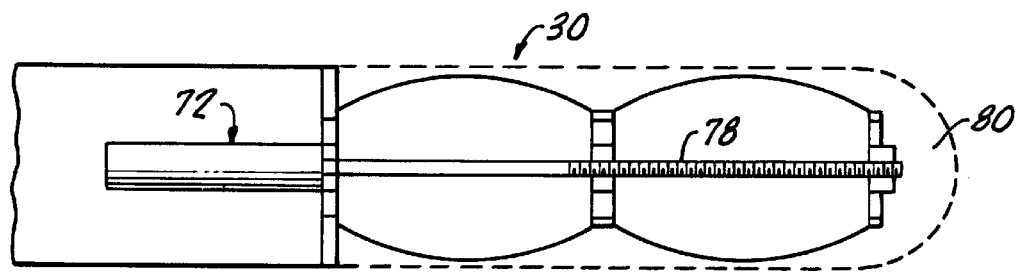
_FIG. 5._
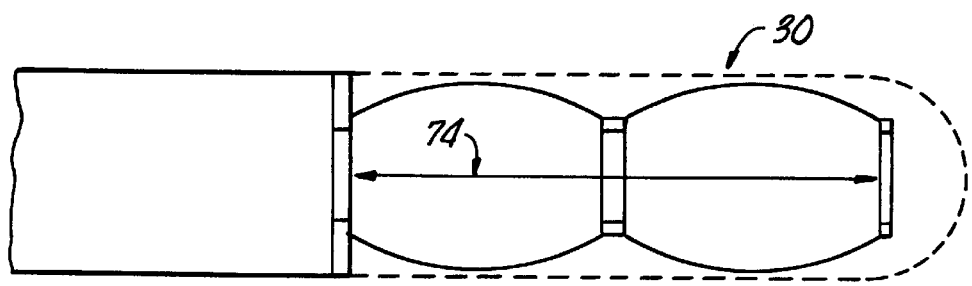
_FIG. 6._

CARDIOVASCULAR MECHANICALLY EXPANDING CATHETER

This application is a continuation application of U.S. Ser. No. 08/804,363 filed Feb. 21, 1997, now abandoned.

The present invention generally relates to surgical devices and more specifically relates to a mechanically expanding catheter apparatus for dilating arteries and other endoluminal anatomic structures and for deployment of intraluminal stents.

Coronary balloon angioplasty catheters are widely used in surgical operations for dilating blocked or clogged human arteries. Such catheters use inflatable balloons which are implanted at the site of a blockage in an uninflated state and are then inflated. The inflated balloon presses the blockage against the vascular wall in order to diminish volume of the blockage and dilate the artery for reestablishing a more healthful blood flow. An intraluminal stent may then be implanted into the artery in order to permanently support the region that has been repaired by the angioplasty. A conventional method of stent deployment consists of disposing the stent in a collapsed state about a deflated angioplasty balloon, inserting the balloon and stent into the vessel and inflating the balloon in order to expand the stent.

While balloon angioplasty is currently leading conventional technology, it includes numerous risks and limitations. For example, during time that a balloon is in an inflated state in the vessel, the presence of the balloon may partially or totally obstruct flow of blood through the vessel, which may cause tissue damage even when the procedure is performed expediently or in small, minor vessels. Complications resulting from this include chest pain, myocardial infarction, cardiac arrhythmia, heart block and ventricular fibrillation. It would therefor be preferable to dilate the clogged vessel without restricting flow of blood through the vessel during the procedure, thus lessening the risk of complication.

Another serious problem with conventional angioplasty techniques is that the balloons frequently do not expand in a uniform manner. Nonuniform expansion of the balloon can lead to a vessel dilation that is less than optimal. On the other hand, if portions of the balloon become overinflated during an arterial dilation procedure, a patient may be left with a weak artery wall and predisposition to vascular dissection.

Notably, balloon expansion is often limited by rigidity of the vessel, particularly if the vessel is calcified. In the presence of calcification, the balloon may rupture during the dilation process because of excessive pressure that is necessary to inflate the balloon against the rigid vessel. In some instances, the balloon may rupture after being pierced by rough or sharp edges of the vascular wall. Complications from balloon rupture may be severe, and include arterial dissection, perforation, vascular bleeding, vascular occlusion and even death.

For these reasons, the present invention was developed for dilating clogged arteries and deployment of stents without the use of any type of an inflatable device. The present invention provides an alternative method for a safe and effective expansion of narrowing in arteries, veins and other endoluminal anatomic structures, as well as for deployment of intraluminal stents.

The advantages of the present invention include a more uniform and controlled stretching of the vessel and unobstructed flow of blood during the dilation procedure. In addition, since a device in accordance with the present invention does not rely on pressure for expansion of a balloon catheter, there is no risk of balloon puncture and rupture within the arterial wall.

SUMMARY OF THE INVENTION

Accordingly, the present invention provides for a safer, more effective surgical apparatus for vessel dilation than conventional balloon angioplasty devices, particularly with respect to repair of occluded arteries. Generally, a cardiovascular mechanically expanding catheter apparatus in accordance with the present invention comprises a mechanically expanding catheter having a distal end sized for insertion into a vessel of a living being. Disposed on the distal end of the catheter is dilation means for pressing against walls of the vessel in order to increase the diameter of the vessel, for example, in order to reestablish a healthy blood flow through an occluded artery. The dilation means includes a mechanical expander which provides means for causing radial expansion of the dilation means against the walls of the vessel upon longitudinal contraction of the mechanical expander. The dilation means is comprised of flexible components and materials in order to allow for smooth passage through the artery during insertion.

Importantly, the apparatus of the present invention does not restrict the flow of blood but enables blood to pass through the expander during the entire surgical procedure. The apparatus does not rely upon inflation for expansion, but rather is mechanically expandable in a way that enables precise control of the amount and speed of expansion during the surgical procedure. Because the apparatus does not restrict the flow of blood at anytime, a physician may have greater leeway in terms of time to work on the patient, compared to conventional techniques. Furthermore, there is no chance of rupture of the device thus eliminating the risk of complications which could result therefrom.

More particularly, the dilation means provides a radial force against vessel walls in response to a physician controlled longitudinal contracting force exerted on the mechanical expander. An actuator is provided for causing the contraction of the expander. In one embodiment, the dilation means may comprise a pair or a series of bellows shaped expanders. In another embodiment, a pair of two layer helically wrapped wire expanders are provided along with a supporting inner tube. In yet another embodiment, similar to the two layer helically wrapped expander embodiment, the dilation means may comprise a flexible screen sleeve.

The actuator for causing the contraction of the expander in the longitudinal direction may comprise a cable mechanism which draws or pulls an end of the expander and causes the expander to arch or project outward, or radially with respect to an axis defined by the catheter. Alternatively, a micromotor or an electrochemical muscle actuator may be provided.

Preferably, means are provided for promoting uniform pressure on vessel walls during the dilation procedure. In particular, the means for promoting uniform pressure may comprise a set of arcuate quadrants disposed about the expander. In addition, a soft elastomer covering, disposed about the expander, provides means for protecting the vessel during insertion and expansion of the apparatus and further functions to return the expander to a non-expanded position when dilation of the vessel has been completed.

BRIEF DESCRIPTION OF THE DRAWINGS

The present invention will be more clearly understood with reference to the following detailed description taken in conjunction with the accompanying drawings of which:

FIG. 5 shows an alternative actuator, namely a micromotor, for causing the contraction of the dilation means;

FIG. 6 shows another alternative actuator, comprising an artificial muscle, for causing contraction of the dilation means;

DETAILED DESCRIPTION

Figure 1:
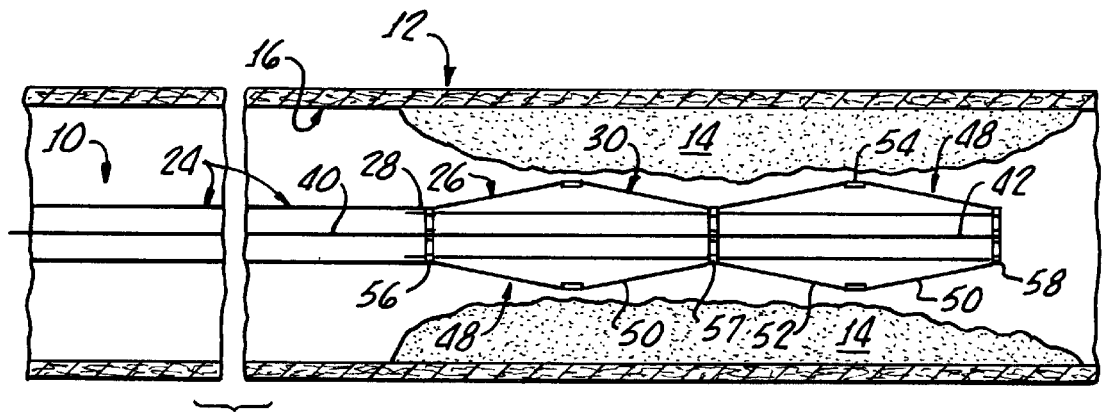
FIG. 1 shows a cross sectional view of a vessel and an embodiment of the present invention, including dilation means comprised of a bellows shaped mechanical expander, prior to actuation thereof, after being positioned adjacent an occlusion in the vessel.

Turning now to FIG. 1, an embodiment 10 of the present invention is shown after being inserted in a vessel 12 that contains an blockage, such as deposits 14 on walls 16 of the vessel 12. As shown, the present invention generally comprises a flexible catheter 24 sized for insertion into the vessel 12 and a mechanically expanding dilating mechanism 26 disposed on a distal end 28 of the catheter 24. The mechanically expanding dilating mechanism 26 provides means for pressing against the blockage 14 and gently stretching the vessel walls 16 as shown in FIG. 2, in order to increase the effective diameter of the vessel 12.

Figure 2:
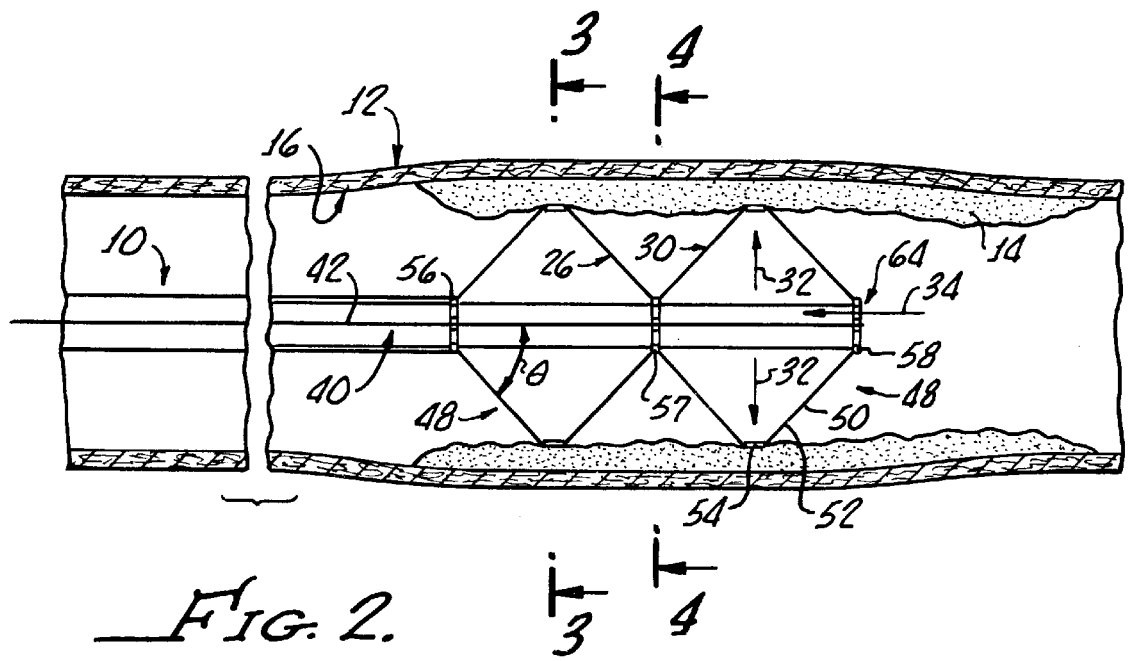
FIG. 2 shows the embodiment of FIG. 1 wherein the mechanical expander has been actuated by means of a cable mechanism in order to mechanically dilate the occluded vessel without restricting flow of blood during the procedure.

More particularly, the dilation means 26 includes a mechanical expander 30 for causing radial expansion of the dilation means 26, in a direction represented by arrows 32, upon contraction of the expander 30 in a longitudinal direction, represented by arrows 34, as shown in FIG. 2.

The present invention also comprises a an actuator 40, for example a cable mechanism 42 which provides means for causing the longitudinal contraction of the expander 30. As will be discussed in detail hereinafter, the present invention was designed to enable controlled dilation of a vessel by converting remotely delivered horizontal, or longitudinal pulling, or contracting, forces into vertical, or radial forces.

The mechanical expander 30 of the present invention 10 shown in FIGS. 1 and 2 will sometimes hereinafter be referred to as a "bellows shaped expander", in order to distinguish this particular embodiment 10 from other alternative embodiments to be discussed hereinafter. In this embodiment, the dilation means 26 preferably comprises a series, or a pair, of adjacent bellow shaped expanders 30 each comprising four wings 50, said wings 50 being disposed equidistantly apart from one another, i.e. at angles of about 90 degrees. For the sake of simplicity, only two wings of each bellow expander 30 are shown, the wings that are shown being in the plane of the drawing of FIGS. 1 and 2. Each wing 50 may be constructed from a pair of miniature struts 52, or wires, flexibly connected together by means of hinges 54.

As shown in FIG. 2, when the device is actuated, the bellows 30 expand in the radial direction compressing the deposits 14 against the vessel walls 16 and immediately improving a flow of blood through the vessel 12. Importantly, unlike a balloon angioplasty procedure which utilizes inflatable balloons to press against walls of an occluded or clogged vessel, the present invention is a permeable, open construction and thus does not hinder the flow of blood during the procedure. Moreover, blood flow through the vessel 12 is improved immediately, without the delay experienced from the use of inflatable devices which temporary cause obstruction of blood flow.

Figure 3:
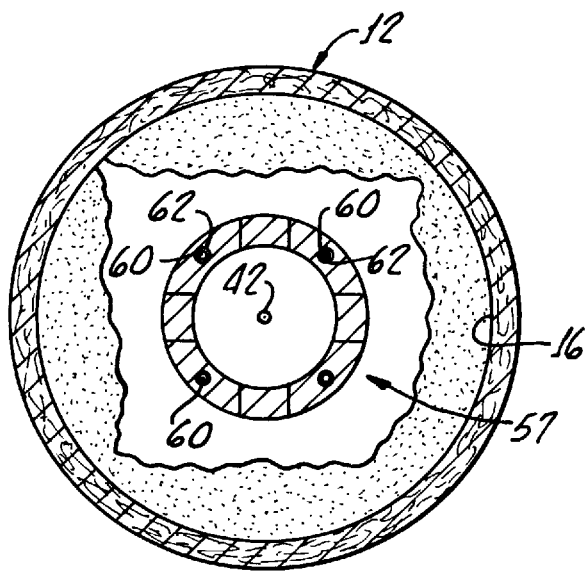
FIG. 3 shows a cross sectional view of the embodiment of FIGS. 1 and 2 taken along line 3—3 of FIG. 2.
Figure 4:
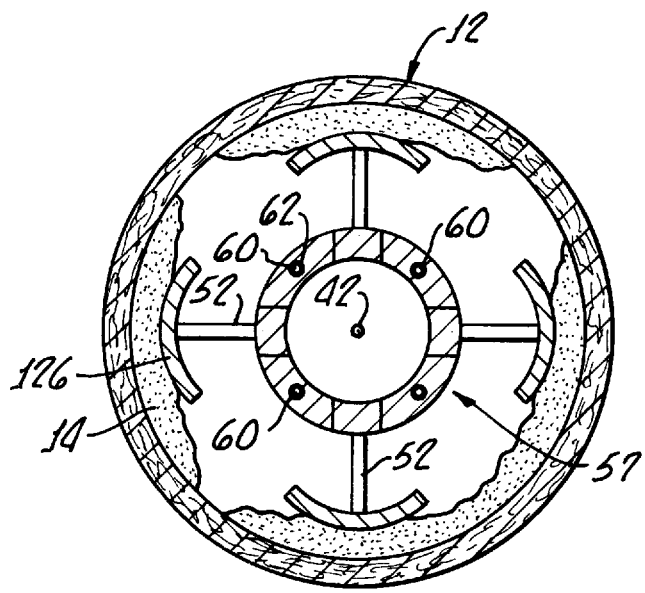
FIG. 4 shows another cross sectional view of the embodiment of FIGS. 1 and 2 taken along line 4—4 of FIG. 2 showing a portion of the vessel being dilated.

Each of the bellow shaped expanders 30 are connected together by means of support rings 56, 57, 58, with support ring 57 being shown in FIGS. 3 and 4. Four longitudinally disposed guide pins 60 are provided through guide apertures 62 in the support rings 56, 57. The guide pins 60 are able to move longitudinally through the apertures 62 in the rings 56 and 57. The guide pins 60 are bonded or welded to the end support ring 58 in order to provide expander rigidity at an end 64 thereof as well as maintain the integrity of the dilation means 26 during storage and in operation. Furthermore, the guide pins 60 provide means for assuring uniformity of contraction of the bellow expanders 30.

In use, the bellows shaped expander 30 can produce strong vertical or radial forces in response to horizontal or longitudinal pulling forces. Calculations of the vertical forces that can be induced by contraction are shown by the tangent function of the pulling force. This indicates that the larger the activated angle between the guide pins 60 and the expander struts 52, the stronger the radial force (unblocking force) that is delivered to the arterial wall 16 by the expander 30. The pulling force is obtained by the displacement differential between the cable 42 which is connected to support ring 58 at the end 64 of the dilation means 26 and the catheter 24.

Using a simple model of the present invention, it can be shown that the pulling force, f, can cause a radial force, F, on the artery wall as follows:

$$F = 2 \cdot f \cdot \tan \theta$$

where $\theta$ is the opening angle of the expander struts 52 with respect to the longitudinal axis.

The cable 42 may be driven manually or mechanically, for example, by a remote spooler (not shown) that pulls on the distal end 64 of the dilation means 26.

As mentioned briefly hereinabove, the actuator 40 may be driven by mechanisms other than the cable 42 shown in FIGS. 1 through 4. For example, alternative actuators may include a micromotor 72 and electrochemical muscle actuators 74, shown in FIGS. 5 and 6.

More specifically, the micromotor 72 may comprise any suitable micromotor, such as, for example, the device under the trademark Minimotor® manufactured by Micromotor Electronics, in Clearwater, Fla. A lead screw 78 connected to the micromotor 72 allows the dilation means 26 to be tightened longitudinally, and thus expanding the bellows 30, using a nut, or other suitable means, at the distal end 64 of the dilating means 26.

Electochemical muscle actuators have been recently developed which may provide an alternative basis for a drive mechanism for contracting the expander 30 by means of electroactive polymers. Such mechanisms are described and disclosed in Reports of New Technology, at the Jet Propulsion Laboratory, which are incorporated herein by specific reference thereto, specifically, Y. Bar-Cohen, B. Joffe and J. Simpson, "Electroactive Muscle Actuators (EMA)", published on Aug. 22, 1996, and Y. Bar-Cohen, T. Xue, Mshahinpoor and S. Lih, "Multi-Finger Electroactive Polymer Gripper (MEPG)" published on Jan. 17, 1997.

Figure 7:
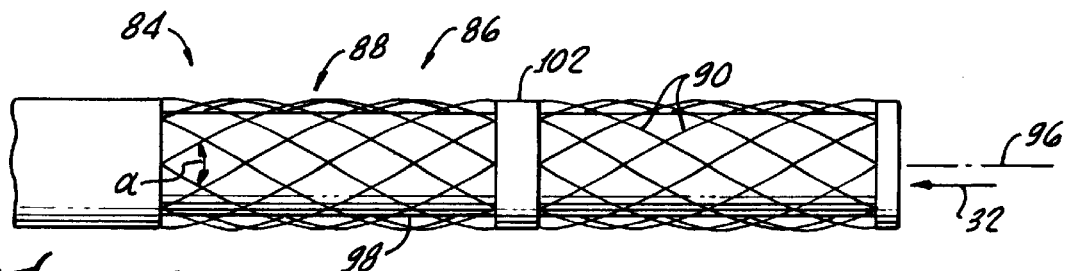
FIG. 7 shows another embodiment of the present invention wherein the dilation means comprises a two layer helically wrapped wire expander.
Figure 8:
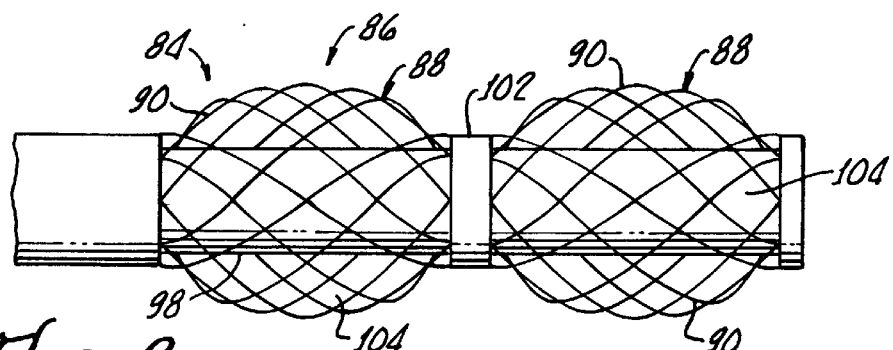
FIG. 8 shows the embodiment of FIG. 7 after the two layer helically wrapped mechanical expander has been actuated by a contraction in the longitudinal direction causing the expansion in the radial direction.

An alternative embodiment 84 to the bellows shaped expander embodiment 10 is shown in FIGS. 7 and 8. In this embodiment 84, the dilation means 86 includes a series of, preferably a pair of, expanders 88, each comprised of two layers of helically wrapped elastic metal wires 90 wrapped in opposite directions at an angle of about 15 to about 30 degrees with respect to the catheter axis 96. The angle of between about 15 to about 30 degrees is selected to optimize the bending moment that leads to the expansion of the two layer set upon a contraction or pulling force on the dilation means 86 in the longitudinal direction 32.

An inner flexible tube 98 may be used as a guide which supports the two layer wrapped expanders 88 and provides means for preventing said expanders 88 from buckling inward. A middle ring sleeve 102 is used to connect together the pair 88. The middle ring sleeve 102 is loosely bound about the inner tube 98 such that it is able to travel longitudinally along the inner tube 98 when the dilating means 86 contracts.

FIG. 8 shows that the dilation means 86 expands into a pair of a smooth arcs upon contraction in the longitudinal direction. The wire construction provides a strong, uniform force against the vessel walls while enabling the flow of blood to continue through interstices 104 of the wires 90 during the procedure.

The wires 90 may be comprised of beryllium, copper, brass, or any other suitable strong, flexible material.

Figure 9:
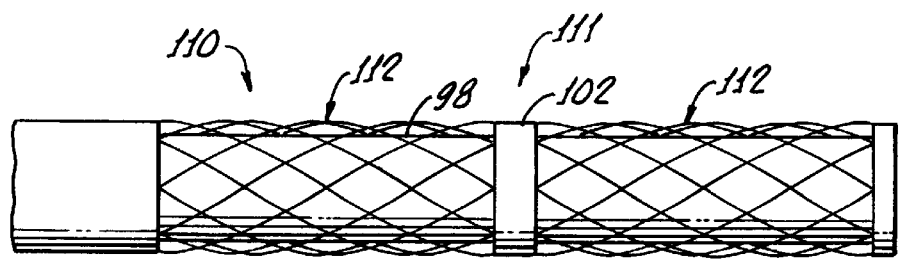
FIG. 9 shows yet another embodiment of the present invention wherein the dilation means comprises a flexible screen sleeve mechanical expander.
Figure 10:
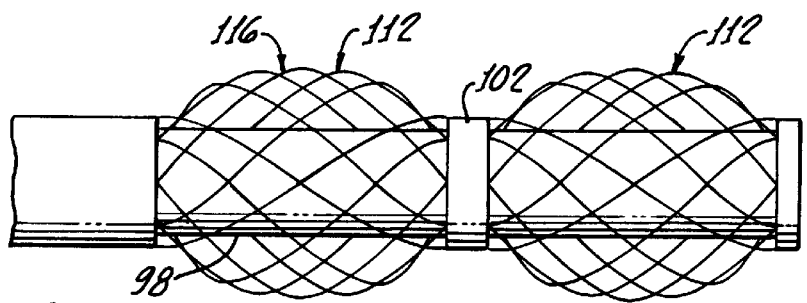
FIG. 10 shows the embodiment of FIG. 9 after the flexible screen sleeve mechanical expander has been expanded against walls of a vessel.

FIGS. 9 and 10 show yet another embodiment 110 of the present invention, similar to the helically wrapped expander embodiment 84 discussed hereinabove. In this embodiment, the dilation means 111 is comprised of at least one, but preferably a pair or more of flexible screen sleeves 112, as an alternative to the bellows shaped expanders 30 or the two layer helical expanders 88.

Similar to the bellows shaped expander 30 and the two layer helically wrapped expander 88, the screen sleeve 112 is a flexible mechanism that expands radially in response to a longitudinal pulling or contracting force. Like the helically wrapped expander embodiment 84, the screen sleeve embodiment 110 preferably includes an inner flexible tube 98 which provides support for the screen sleeve 112 and prevents the flexible screen sleeve 112 from buckling inward. In addition, a support ring 102 is provided which is slidably disposed about the inner tube 98 and connects adjacent screen sleeves 112.

While these two latter embodiments 84, 110 are different in structure from the bellows shaped embodiment 10, their principle of operation is similar thereto. All of the dilation means, 26, 86, 111 of the various embodiments expand radially in response to a pulling or contracting force in the longitudinal direction and do not interfere with fluid flow during the surgical procedure. The permeable, mechanical expanders 30, 84, 112 allow unobstructed fluid flow through the dilation means 26, 86, 111 during the radial expansion. However, rather than forming a series of V-shaped projections upon the contraction, as the bellows shaped expander embodiment 10, the two layer helical wrapping and the screen sleeve embodiments 84, 110 form a series of arcs.

It should be appreciated that other alternative expanders are possible. For example, rather than the screen sleeve described hereinabove, an elastomer sleeve may be provided. Squeezing or contracting of the rubber sleeve in the longitudinal direction will cause a lateral or radial expansion, in which the level of radial expansion may be at least half the percentage of the longitudinal contraction. The level of squeezing required to cause the necessary radial expansion for vessel dilation will depend on elasticity of the elastomer sleeve material, which is preferably selected to sustain minimum compressibility while producing the radial expansion.

Figure 11:
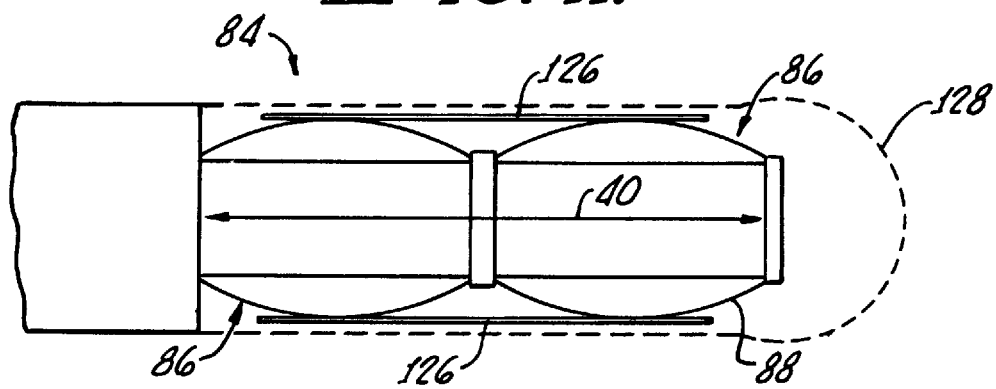
FIG. 11 shows the present invention including quadrates providing means for promoting uniform pressure against vessel walls and further including an elastomer covering providing means for protecting vessel walls during the dilation procedure.
Figure 12:
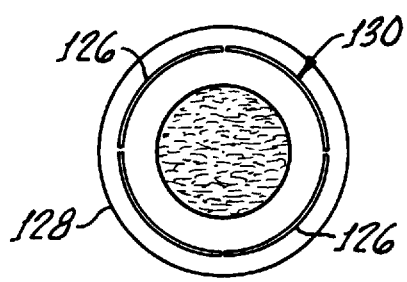
FIGS. 12 and 13 shows cross-sectional views of the present invention including the quadrates and elastomer covering, where the dilation means is in non-expanded and expanded positions, respectively.
Figure 13:
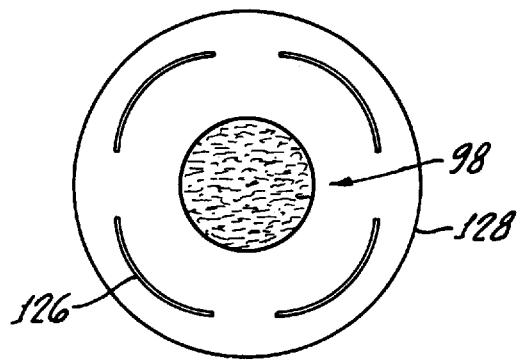

Additional features of the present invention are shown in FIGS. 11 through 13. For the sake of simplicity, the features will be discussed with respect to only one of the embodiments, though it should be appreciated that they are applicable to all of the embodiments. In particular, FIGS. 11 through 13 show the two layer helically wrapped embodiment 84 of the present invention wherein the dilation means 86 includes quadrates 126 disposed tangentially with respect to the expanders 88, for promoting uniform pressure against vessel walls (not shown) and further including an elastomer covering 128 which provides means for protecting vessel walls during the dilation procedure.

Figure 14:
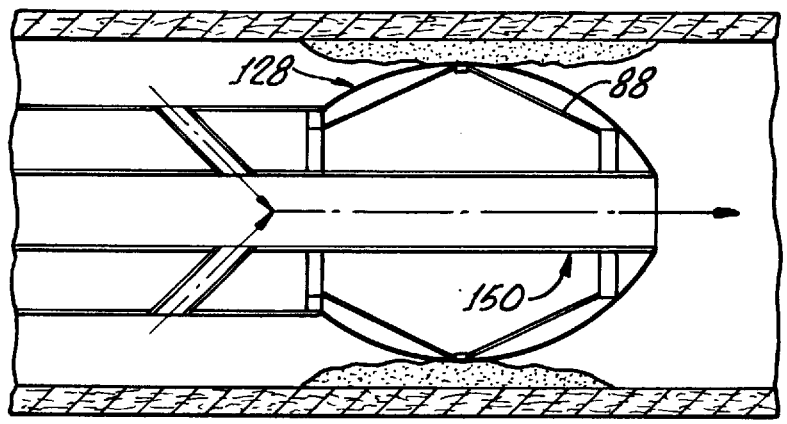
FIG. 14 shows a cross sectional view of the present invention in which the elastomer covering is permeable and forms an inner passageway for providing continuous blood flow during the procedure.

More particularly, the quadrates 126 may comprise four portions 128 of a tube structure 130, as shown most clearly in cross sectional views FIGS. 13 and 14, clamped or otherwise suitably connected, to the expander 88 in such a way as to allow expansion of the expander 88 while maintaining the rigidity of the quadrates 126.

For example, the quadrates 126 are preferably configured to contact each other when the dilation means 86 is in a closed position, such as shown in FIG. 12, to form said tube structure 130 about the expander 88. In this way, the quadrates 126 will function in part to provide additional strength and support to the dilation means 86 during its insertion into the vessel (not shown).

Upon expansion of the dilation means 86, the quadrates 126 separate with respect to each other, as shown in FIG. 4 and FIG. 13, as they are pushed toward the vessel wall. The quadrates 126 function to evenly distribute pressure from the expanders 88 to the vessel wall in order to optimize the effectiveness and safety of the dilation procedure. In addition, the quadrates 126 promote delivery of even forces over a wide area of the vessel wall and promote uniform stretching thereof.

In addition, the elastomer covering 128 feature of the present invention may be used as a means of protecting the vessel during insertion and expansion of the device. The covering 128 is comprised of a soft material having sufficient elasticity to close the dilation means 86 prior to withdrawal of the catheter apparatus from the vessel. In other words, the covering 128 provides a means for biasing the expander in a closed, non-expanded position.

Referring now to FIG. 14, the elastomer covering 128 may be made of a permeable material. In addition, the permeable, elastomer covering 128 may be disposed as to surround the expander 88 forming an inner tube 150 coaxial to the expander 88 and through the center thereof in order to provide a passageway for enhancing a continuous flow of blood in the patient while the vessel is being treated.

It should be appreciated that although the mechanically expanding catheter has been described hereinabove with primary emphasis on unblocking of clogged vessels such as arteries, the present invention is also useful for the dilation of other endoluminal narrowing or strictures and for deployment of intraluminal stents.

Although there has been hereinabove described a cardiovascular mechanically expanding catheter in accordance with the present invention, for the purpose of illustrating the manner in which the invention may be used to advantage, it will be appreciated that the invention is not limited thereto. Accordingly, all modifications, variations, or equivalent arrangements which may occur to those skilled in the art should be considered to be within the scope of the invention as defined in the appended claims.

What is claimed is:

1. Catheter apparatus for unblocking occluded vessels and delivering stents, said catheter apparatus comprising:

a catheter defining a longitudinal axis and having a distal end sized for insertion into a vessel in a living being;

mechanically expanding dilation means, disposed on the catheter distal end, for pressing against walls of the vessel in order to cause an increase in a diameter of the vessel, said dilation means including mechanical expander means for causing radial expansion of the dilation means upon contraction of expander means in a longitudinal direction, said mechanically expanding dilation means comprising a plurality of pairs of adjacent bellow shaped expanders, each pair of expanders being interconnected by a support ring, each of the plurality of pairs being disposed in an equidistant angular relationship around the longitudinal axis, each expander having two pairs of opposing wings with each pair of wings being connected to one another by hinges; and actuator means for causing the longitudinal contraction of the expander means.

2. The apparatus according to claim 1 wherein the dilation means includes quadrate means, disposed about the expander means, for promoting uniform pressure on the walls of the vessel.

3. The apparatus according to claim 1 wherein the actuator means comprises a cable.

4. The apparatus according to claim 1 wherein the actuator means comprises a micromotor.

5. The apparatus according to claim 1 wherein the actuator means comprises an artificial muscle.

6. Catheter apparatus for unblocking occluded vessels and delivering stents, said catheter apparatus comprising:

a catheter having a distal end sized for insertion into a vessel in a living being mechanically expanding dilation means, disposed on the catheter distal end, for pressing against walls of the vessel in order to cause an increase in a diameter of the vessel, said mechanically expanding dilation means including permeable mechanical expander means for causing radial expansion of the dilation means upon contraction of expander means in a longitudinal direction said permeable mechanical expander means allowing unobstructed fluid flow through the dilation means during the radial expansion thereof, said mechanically expanding dilation means comprising a plurality of pairs of adjacent bellow shaped expanders, each pair of expanders being interconnected by a support ring, each of the plurality of pairs being disposed in an equidistant angular relationship around the longitudinal axis, each expander having two pairs of opposing wings with each pair of wings being connected to one another by hinges; and actuator means for causing the longitudinal contraction of the expander means.

7. The apparatus according to claim 6 wherein the dilation means includes quadrate means, disposed about the expander means, for promoting uniform pressure on the walls of the vessel.

8. The apparatus according to claim 6 wherein the actuator means comprises a cable.

9. The apparatus according to claim 6 wherein the actuator means comprises a micromotor.

10. The apparatus according to claim 6 wherein the actuator means comprises an artificial muscle.

* * * * *